(12) United States Patent
Ehm et al.

(10) Patent No.: US 9,096,674 B2
(45) Date of Patent: Aug. 4, 2015

(54) ANTIBODIES FOR DETERMINING THE PROTHROMBIN FRAGMENT F2/F1+2 IN A HOMOGENEOUS IMMUNOASSAY

(75) Inventors: Matthias Ehm, Munich (DE); Bodo Fischer, Marburg (DE); Harald Althaus, Wetter (DE); Roland Barten, Marburg (DE); Stefan Teigelkamp, Niederwalgern (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 1211 days.

(21) Appl. No.: 12/566,464

(22) Filed: Sep. 24, 2009

(65) Prior Publication Data
US 2010/0081212 A1    Apr. 1, 2010

(30) Foreign Application Priority Data
Sep. 30, 2008 (DE) .......... 10 2008 049 601

(51) Int. Cl.
| | |
|---|---|
| C07K 16/36 | (2006.01) |
| C07K 16/42 | (2006.01) |
| C12N 5/20 | (2006.01) |
| C12P 21/08 | (2006.01) |
| G01N 33/563 | (2006.01) |
| G01N 33/573 | (2006.01) |
| G01N 33/86 | (2006.01) |
| C12N 9/74 | (2006.01) |

(52) U.S. Cl.
CPC .............. *C07K 16/36* (2013.01); *C07K 16/42* (2013.01); *C12N 9/6429* (2013.01); *C12Y 304/21005* (2013.01); *G01N 33/563* (2013.01); *G01N 33/573* (2013.01); *G01N 33/86* (2013.01); *C07K 2317/32* (2013.01); *C07K 2319/00* (2013.01); *G01N 2333/96463* (2013.01)

(58) Field of Classification Search
CPC .... C07K 16/36; C07K 16/42; C07K 2317/32; C07K 2319/00; C12N 9/6429; C12Y 304/21005; G01N 33/86; G01N 2333/96463; G01N 33/563; G01N 33/573
USPC ........ 435/7.1, 7.4, 7.92, 7.94, 13, 70.21, 452, 435/337, 345, 962, 975; 436/507, 512, 518, 436/547, 548, 69; 530/381, 388.25, 388.9, 530/389.3, 389.8, 391.1, 391.3, 806, 807, 530/866
See application file for complete search history.

(56) References Cited

U.S. PATENT DOCUMENTS

| | | | | |
|---|---|---|---|---|
| 4,544,640 | A | * | 10/1985 | Soma et al. ............... 436/506 |
| 4,670,383 | A | * | 6/1987 | Baier et al. .............. 435/7.92 |
| 4,840,895 | A | * | 6/1989 | Self ........................ 435/7.92 |
| 4,956,303 | A | * | 9/1990 | Self ........................ 436/542 |
| 5,223,441 | A | * | 6/1993 | Ullman et al. ........... 436/547 |
| 5,480,792 | A | * | 1/1996 | Buechler et al. ......... 435/6.16 |
| 5,830,681 | A | | 11/1998 | Hursting et al. |
| 6,541,275 | B1 | | 4/2003 | Ruiz et al. |
| 6,566,085 | B1 | | 5/2003 | Pelzer et al. |
| 7,749,712 | B2 | * | 7/2010 | Pulli et al. ................. 435/7.1 |
| 7,795,403 | B2 | | 9/2010 | Teigelkamp et al. |
| 2003/0219845 | A1 | | 11/2003 | Ruiz et al. |
| 2004/0053372 | A1 | | 3/2004 | Pelzer et al. |
| 2005/0113562 | A1 | | 5/2005 | Teigelkamp et al. |

FOREIGN PATENT DOCUMENTS

| | | |
|---|---|---|
| EP | 0 264 219 A2 | 4/1988 |
| EP | 0 303 983 A2 | 2/1989 |
| EP | 0 475 784 A1 | 3/1992 |
| EP | 1 541 676 A1 | 6/2005 |
| WO | WO 85/04422 A1 | 10/1985 |
| WO | WO 87/07147 A1 | 12/1987 |

OTHER PUBLICATIONS

Walz et al.; "Amino Acid Sequence of Human Prothrombin Fragments 1 and 2", Proc. Natl. Acad. Sci. USA, Biochemistry, vol. 74, No. 5, pp. 1969-1972, (1977).

* cited by examiner

*Primary Examiner* — Gail R Gabel
*Assistant Examiner* — James L Grun
(74) *Attorney, Agent, or Firm* — Finnegan, Henderson, Farabow, Garrett & Dunner, L.L.P.

(57) ABSTRACT

The present invention is in the area of coagulation analysis and relates to antibodies which bind specifically to an immune complex of prothrombin fragment F2/F1+2 and an F2/F1+2 neoepitope-specific antibody fragment, and to the preparation and the use thereof in methods for determining F2/F1+2.

18 Claims, 1 Drawing Sheet

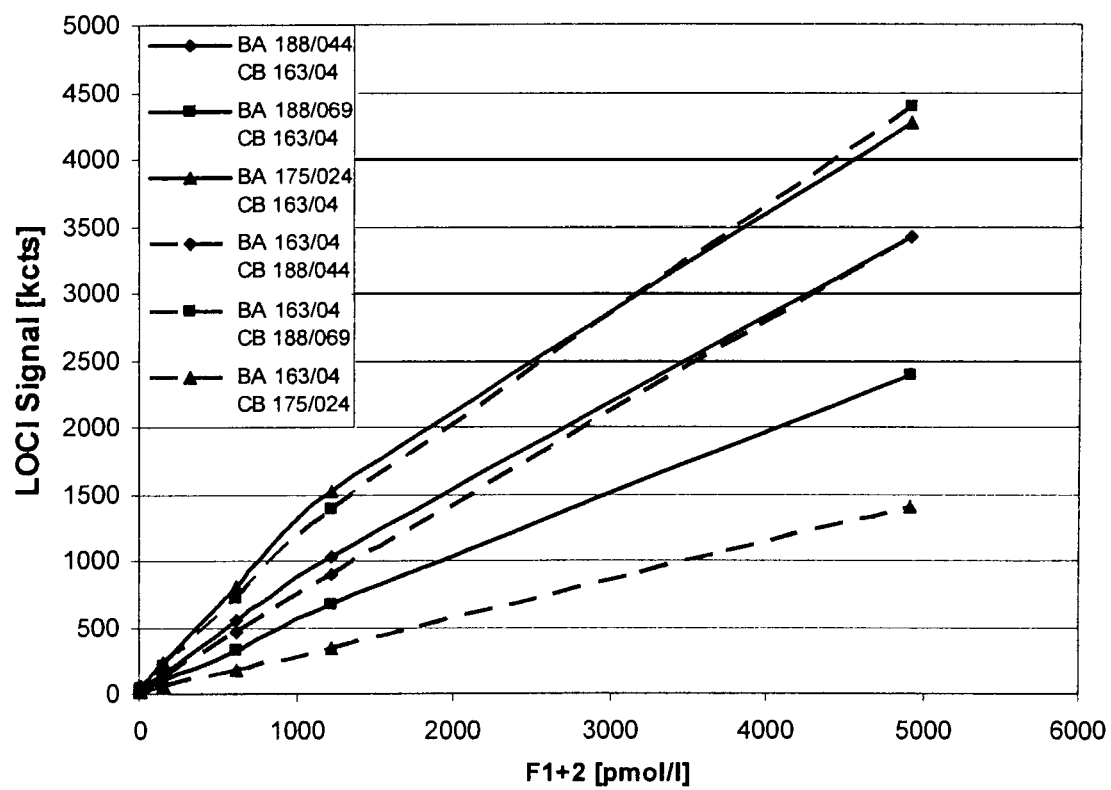

SEQUENCE LISTING

```
<160> NUMBER OF SEQ ID NOS: 3

<210> SEQ ID NO 1
<211> LENGTH: 4
<212> TYPE: PRT
<213> ORGANISM: Homo sapiens

<400> SEQUENCE: 1

Ile Glu Gly Arg
1

<210> SEQ ID NO 2
<211> LENGTH: 10
<212> TYPE: PRT
<213> ORGANISM: Homo sapiens

<400> SEQUENCE: 2

Cys Gly Ser Asp Arg Ala Ile Glu Gly Arg
1               5                   10

<210> SEQ ID NO 3
<211> LENGTH: 15
<212> TYPE: PRT
<213> ORGANISM: Homo sapiens

<400> SEQUENCE: 3

Cys Leu Asp Glu Asp Ser Asp Glu Glu Arg Ala Ile Glu Gly Arg
1               5                   10                  15
```

ANTIBODIES FOR DETERMINING THE PROTHROMBIN FRAGMENT F2/F1+2 IN A HOMOGENEOUS IMMUNOASSAY

CROSS-REFERENCE TO RELATED APPLICATIONS

This application claims priority to German Application No. 10 2008 049 601.4 filed on Sep. 30, 2008, which is incorporated herein by reference.

The present invention is in the area of coagulation analysis and relates to antibodies which bind specifically to a complex of F2/F1+2 and an F2/F1+2-specific binding partner, and to the preparation thereof and to the use thereof in methods for determining F2/F1+2.

A large number of diagnostically relevant parameters are available for clinical assessment of the status of a patient's coagulation system. In particular, quantitative detection of so-called activation markers of coagulation makes it possible to assess the coagulation or fibrinolysis process. Determination of the prothrombin fragment F2/F1+2 in a patient's sample makes it possible to detect or preclude increased thrombin formation in vivo and is employed for example for revealing intravascular thrombin formation in a consumption coagulopathy, in acute venous thromboembolisms or in arterial vessel occlusions (myocardial infarction, cerebral infarction) or for monitoring anticoagulant therapies.

Prothrombin is the proenzyme of thrombin, the central enzyme of the coagulation cascade. The prothrombin protein has a modular structure and consists of an N-terminal F1+2 portion and of a C-terminal thrombin portion. Prothrombin is cleaved by the proteolytic activity of factor Xa to produce from each prothrombin molecule (70 kD) a thrombin molecule (30 kD) with release of a prothrombin fragment F1+2 (35-37 kD). Cleavage of the fragments F1 (23 kDa) and F2 (14 kDa) is moreover possible through the autocatalytic cleavage of prothrombin by thrombin. Since thrombin does not occur in free form in the blood, but is bound to inhibitors and to fibrin immediately after its formation, the extent of thrombin formation must be ascertained indirectly, e.g. by determining the activation markers F1+2 and/or F2. One possibility for detecting or precluding an increased thrombin formation in vivo is accordingly determination of the F2/F1+2 concentration in the plasma.

A general difficulty with F2/F1+2 assays is that prothrombin is present in the sample in a 1000 to 10 000-fold molar excess compared with F2/F1+2. Immunological detection of F2/F1+2 in the presence of prothrombin is impeded by the fact that the liberated prothrombin fragments F2/F1+2 have, by comparison with intact, uncleaved prothrombin, only a single F2/F1+2-specific antigenic epitope, specifically the carboxy terminus of the F2/F1+2 peptide (neoepitope) produced by thrombin cleavage. Only antibodies directed against the carboxy-terminal region of the F2/F1+2 peptide are able to bind specifically to the prothrombin fragments F2/F1+2 without at the same time showing a specificity for intact prothrombin. All other antigenic determinants of the F2/F1+2 fragment are likewise specific for intact prothrombin.

The preparation of specific F2/F1+2 antibodies which do not bind to prothrombin is described for example in EP 303 983 A2 (Pelzer et al.), in U.S. Pat. No. 5,830,681 (Hursting et al.) or in U.S. 2003/0219845 A1 (Ruiz et al.). It is important for the specificity of the anti-F2/F1+2 antibodies that they bind to an epitope which comprises at least the four carboxy-terminal amino acids of the F2/F1+2 fragments (Ile-Glu-Gly-Arg-OH) (SEQ ID NO:1). Since sandwich immunoassays are ordinarily employed for determining the F2/F1+2 concentration, two anti-F2/F1+2 antibodies are required. EP 1 541 676 A1 (Teigelkamp et al.) describes antibodies which bind to one epitope on the N-terminal half of the F2 fragment and thus also to intact prothrombin, but are particularly suitable for use as secondary antibodies in combination with the F2/F1+2 neoepitope-specific primary antibodies in a sandwich immunoassay.

The known antibodies are suitable for determining the F2/F1+2 concentration in plasma samples in heterogeneous immunoassays, preferably in the form of a sandwich ELISA method. For this purpose, the F2/F1+2 neoepitope-specific antibodies ("primary antibodies") are coupled to a solid phase and incubated with the sample so that the F2/F1+2 peptides are able to bind to the immobilized antibodies. Unbound proteins, especially prothrombin, are removed by a washing step, before the second, F2/F1+2- and prothrombin-binding antibody ("secondary antibody") is applied by adding an antibody solution. This second antibody is ordinarily associated with a signal-generating component which permits quantification of the F2/F1+2 concentration.

However, there are only limited possibilities for designing a direct, homogeneous sandwich immunoassay without washing or separating steps with the monoclonal antibodies known in the prior art because, in the homogeneous assay design, the F2/F1+2- and prothrombin-binding secondary antibody is mostly bound by the prothrombin present in the sample and is thus no longer available for sandwich formation with the analyte F2/F1+2, which is indispensable for signal generation.

The present invention was thus based on the object of providing means which make it possible to determine F2/F1+2 in samples which contain prothrombin in excess specifically in a homogeneous binding assay.

The object is achieved by providing the means and methods of the invention which are described in the claims.

The object is achieved in particular by providing a monoclonal antibody which binds specifically to an immune complex which comprises prothrombin fragment F2/F1+2 to which an antibody or an antibody fragment with specificity for the carboxy-terminal neoepitope of the prothrombin fragment F2/F1+2 is bound, and where the antibody does not, however, bind to the prothrombin fragment F1+2 or F2 alone and does not bind to the antibody or the antibody fragment with specificity for the carboxy-terminal neoepitope of the prothrombin fragment F2/F1+2 alone.

Antibodies with specificity for immune complexes which consist of an analyte to which an analyte-specific binding partner, e.g. a primary antibody or a primary antibody fragment, is bound are known in principle, e.g. from EP 264 219 A2, EP 475 784 A1, WO 85/04422 A1 or WO 87/07147. However, in relation to the present invention it has surprisingly been found that in order to obtain an antibody of the invention with specificity for a prothrombin fragment F2/F1+2-binding partner immune complex it is necessary to use as immunizing antigen an immune complex which comprises a peptide which includes at least the complete prothrombin fragment F2 to which an antibody fragment with specificity for the carboxy-terminal neoepitope of the prothrombin fragment F2/F1+2 is bound. It was not possible to generate antibodies with specificity for the immune complex using immune complexes which comprised only a fragment of the F2 prothrombin fragment, and with immune complexes which comprised a complete antibody with specificity for the carboxy-terminal neoepitope of the prothrombin fragment F2/F1+2.

The present invention relates to an isolated, purified immune complex comprising a peptide which includes at least the complete prothrombin fragment F2 to whose carboxy terminus an antibody fragment with specificity for the carboxy-terminal neoepitope of the prothrombin fragment F2/F1+2 is bound.

A peptide which includes at least the complete prothrombin fragment F2, i.e. amino acid residues 156-273 of human prothrombin (see, for example, FIG. 1 in Walz, D. A. (1977) Amino acid sequence of human prothrombin fragments 1 and 2. Proc. Natl. Acad. Sci. USA Vol. 74, No. 5, 1969-1972), and which has the carboxy-terminal neoepitope of the prothrombin fragment F2/F1+2 can be obtained for example by incubating a prothrombin-containing solution with factor Xa or by activating the coagulation cascade in a coagulation factor-containing solution, for example with the snake venom Russell's Viper Venom (RVV), and subsequently purifying the F2 fragment by chromatography. Alternatively, the prothrombin fragment F2 can be obtained synthetically by chemical synthesis or recombinantly by expression in a prokaryotic or eukaryotic expression system.

All peptides which include at least the complete prothrombin fragment F2, including the carboxy-terminal neoepitope, i.e. also the complete prothrombin fragment F1+2 and the various amino-terminally truncated F1+2 fragments, are suitable.

Suitable antibody fragments with specificity for the carboxy-terminal neoepitope of the prothrombin fragment F2/F1+2, such as, for example, Fab, Fab', F(ab')$_2$ or Fv fragments, can be obtained for example recombinantly or by means of enzymatic cleavage of antibodies, preferably of monoclonal antibodies, the antibodies being specific for the carboxy-terminal neoepitope of the prothrombin fragment F2/F1+2 and not binding to prothrombin. Such F2/F1+2-specific antibodies which do not bind to prothrombin are described for example in EP 303 983 A2 (Pelzer et al.), in U.S. Pat. No. 5,830,681 (Hursting et al.) or in US 2003/0219845 A1 (Ruiz et al.). Enzymatic cleavage of monoclonal antibodies can be carried out for example by means of papain, pepsin or ficin. Particularly preferred antibody fragments are Fab fragments which can be obtained for example by means of enzymatic cleavage by papain.

Very particularly preferred antibody fragments are fragments, especially Fab fragments, of the monoclonal, F2/F1+2 neoepitope-specific antibody 96-163/04 which was prepared according to the teaching in U.S. Pat. No. 5,830,681 (Hursting et al., especially examples I-VI) using a synthetic peptide with the sequence Cys-Gly-Ser-Asp-Arg-Ala-Ile-Glu-Gly-Arg-OH ("PF2") (SEQ ID NO:2) as immunizing antigen and which is produced by a hybridoma cell line which was deposited on Jun. 3, 2008, at the DSMZ-Deutsche Sammlung von Mikroorganismen und Zellkulturen GmbH, Inhoffenstraßβe 7B, 38124 Brunswick, Germany, under accession number DSM ACC2911.

The immune complex of the invention is prepared by mixing, and incubating under suitable conditions, the peptide which includes at least the complete prothrombin fragment F2, and the antibody fragment with specificity for the carboxy-terminal neoepitope of the prothrombin fragment F2/F1+2 to form the immune complex. Subsequently, the immune complex is separated from the other reactants, i.e. isolated and purified, preferably by chromatography.

In a preferred embodiment of the immune complex of the invention, the complex is chemically crosslinked, preferably by treating the complex with an aldehyde such as, for example, glutaraldehyde or formaldehyde.

A further preferred embodiment of the immune complex of the invention relates to a complex which is coupled to a carrier protein such as, for example, keyhole limpet hemocyanin or ovalbumin. The immunostimulatory effect of such carrier proteins and methods for coupling them are known in the state of the art.

A further aspect of the present invention relates to the use of an immune complex of the invention as immunizing antigen in a method for obtaining monoclonal antibodies which specifically bind the complex, but not the individual components of the complex. Methods for obtaining monoclonal antibodies are sufficiently well known, such as, for example, the establishment of hybridoma cells with subsequent purification of the secreted antibodies.

The invention further relates to monoclonal antibodies which are distinguished in that they bind to an immune complex comprising a peptide which includes at least the complete prothrombin fragment F2, to which an antibody fragment with specificity for the carboxy-terminal neoepitope of the prothrombin fragment F2/F1+2 is bound, but not to the prothrombin fragment F2 alone and not to the antibody fragment with specificity for the carboxy-terminal neoepitope of the prothrombin fragment F2/F1+2 alone.

Particularly preferred antibodies in the context of the present invention are antibodies which specifically bind to an immune complex which comprises the complete F2 peptide, to which an Fab fragment of a monoclonal antibody formed by the hybridoma cell line DSM ACC 2911 is bound. Such antibodies are produced for example by the hybridoma cell lines 2006-175/024, 2006-188/044 or 2006-188/069. These hybridoma cell lines were deposited on Jun. 3, 2008, at the DSMZ—Deutsche Sammlung von Mikroorganismen and Zellkulturen GmbH, Inhoffenstraße 7B, 38124 Brunswick, Germany, under the accession numbers DSM ACC2912, DSM ACC2913 and DSM ACC2914.

This invention also relates to an antibody of the invention which is associated with a solid phase and/or a component of a signal-generating system.

The term "solid phase" for the purposes of this invention comprises an article which consists of porous and/or nonporous, usually water-insoluble material, and which may have a wide variety of shapes, such as, for example, vessel, tube, microtiter plate, bead, microparticle, rod, strip, filter paper or chromatography paper, etc. The surface of the solid phase is usually hydrophilic or can be made hydrophilic. The solid phase may consist of a wide variety of materials such as, for example, of inorganic and/or of organic materials, of synthetic, of naturally occurring and/or of modified naturally occurring materials. Examples of solid phase materials are polymers such as, for example, cellulose, nitrocellulose, cellulose acetate, polyvinyl chloride, polyacrylamide, crosslinked dextran molecules, agarose, polystyrene, polyethylene, polypropylene, polymethacrylate or nylon; ceramic, glass, metals, especially noble metals such as gold and silver; magnetite, mixtures or combinations thereof, etc.

The solid phase may have a coating composed of one or more layers, e.g. of proteins, carbohydrates, lipophilic substances, biopolymers, organic polymers or mixtures thereof, in order for example to diminish or prevent nonspecific binding of constituents of the sample to the solid phase, or in order for example to achieve improvements in relation to the suspension stability of particulate solid phases, the storage stability, the shaping stability or the resistance to UV light, microbes or other agents having a damaging effect.

A "signal-generating system" may comprise one or more components, where at least one component comprises a detectable label. A label means any molecule which itself produces a signal or can induce the production of a signal such as, for example, a fluorescent substance, a radioactive substance, an enzyme, or a chemiluminescent substance. The signal can be detected or measured for example on the basis of the enzymic activity, the luminescence, the light absorption, the light scattering, the emitted electromagnetic or radioactive radiation, or a chemical reaction.

A label is able itself to generate a detectable signal, so that no further components are necessary. Many organic molecules absorb ultraviolet and visible light, and the energy transferred by the absorption of light can put these molecules into an excited energy state, and they emit the absorbed energy in the form of light of a different wavelength from that of the incident light. Other labels in turn are able to generate directly a detectable signal, such as, for example, radioactive isotopes or dyes.

Other labels in turn require further components to generate the signal, i.e. the signal-producing system includes in such a case all the components required for signal generation, such as, for example, substrates, coenzymes, quenchers, accelerators, additional enzymes, substances which react with enzyme products, catalysts, activators, cofactors, inhibitors, ions, etc.

Suitable labels are, for example, enzymes including horseradish peroxidase, alkaline phosphatase, glucose-6-phosphate dehydrogenase, alcohol dehydrogenase, glucose oxidase, β-galactosidase, luciferase, urease and acetylcholinesterase; dyes; fluorescent substances including fluorescein isothiocyanate, rhodamine, phycoerythrin, phycocyanin, ethidium bromide, 5-dimethylaminonaphthalene-1-sulfonyl chloride and fluorescent chelates of rare earths; chemiluminescent substances including luminol, isoluminol, acridinium compounds, olefin, enol ether, enamine, aryl vinyl ether, dioxene, arylimidazole, lucigenin, luciferin and aequorin; sensitizers including eosin, 9,10-dibromoanthracene, methylene blue, porphyrin, phthalocyanin, chlorophyll, Rose Bengal; coenzymes; enzyme substrates; radioactive isotopes including $^{125}I$, $^{131}I$, $^{14}C$, $^{3}H$, $^{32}P$, $^{35}S$, $^{14}C$, $^{51}Cr$, $^{59}Fe$, $^{57}Co$ and $^{75}Se$; particles including magnetic particles or particles, preferably latex particles, which themselves may be labeled for example with dyes, sensitizers, fluorescent substances, chemiluminescent substances, isotopes or other detectable labels; sol particles including gold or silver sols, etc.

A signal-generating system may also include components which are able to engage in a detectable interaction when spatially close to one another, e.g. in the form of energy donors and energy recipients such as, for example, photosensitizers and chemiluminescent substances (see, e.g. EP 515 194 A2), photosensitizers and fluorophores (WO 95/06877), radioactive iodine-125 and fluorophores (Udenfriend, S. et al. (1985) Proc. Natl. Acad. Sci. 82:8672-8676), fluorophores and fluorophores (Mathis, G. (1993) Clin. Chem. 39:1953-1959) or fluorophores and fluorescence quenchers (U.S. Pat. No. 3,996,345). An interaction between the components includes direct transfer of energy between the components, e.g. by emission of light or electrons, and via short-lived reactive chemical molecules. Also included thereby are processes in which the activity of one component is inhibited or enhanced by one or more others, for example inhibiting or increasing enzymic activity or inhibiting, increasing or altering (e.g. wavelength shift, polarization) the electromagnetic radiation emitted by the influenced component. The interaction between the components also includes enzyme cascades. In this case, the components are enzymes, at least one of which provides the substrate for another, so that a maximum or minimum reaction rate of the coupled substrate conversion results.

An efficient interaction between the components usually takes place when they are spatially adjacent, i.e. for example within a range of distance of a few μm, in particular within a range of distance of below 600 nm, preferably below 400 nm, very particularly preferably of below 200 nm.

Microparticles are frequently used as solid phase and/or as label. The term "microparticles" means for the purposes of this invention particles which have an approximate diameter of not less than 20 nm and not more than 20 μm, normally between 40 nm and 10 μm, preferably between 0.1 and 10 μm, particularly preferably between 0.1 and 5 μm, very particularly preferably between 0.15 and 2 μm. The microparticles may have regular or irregular shapes. They may be spheres, spheroids, spheres with larger or smaller cavities or pores. The microparticles may consist of organic or inorganic material or of a mixture or combination of the two. They may also consist of a porous or nonporous, a swellable or nonswellable material. The microparticles can in principle have any density, but particles having a density close to the density of water, such as about 0.7 to about 1.5 g/ml, are preferred. The preferred microparticles can be suspended in aqueous solutions and are maximally stable in suspension. They may be transparent, partially transparent or opaque. The microparticles may consist of a plurality of layers such as, for example, the so-called core-and-shell particles having a core and one or more enveloping layers. The term microparticle includes for example dye crystals, metal sols, silica particles, glass particles, magnetic particles, polymer particles, oil drops, lipid particles, dextran, and protein aggregates. Preferred microparticles are particles which can be suspended in aqueous solutions and consist of water-insoluble polymer material, in particular of substituted polyethylenes. Latex particles are very particularly preferred, for example composed of polystyrene, acrylic acid polymers, methacrylic acid polymers, acrylonitrile polymers, acrylonitrile-butadiene-styrene, polyvinyl acetate-acrylate, polyvinylpyridine, vinyl chloride-acrylate. Latex particles having reactive groups on their surface such as, for example, carboxyl, amino or aldehyde groups allowing covalent linkage for example of specific binding partners to the latex particles are of particular interest. The preparation of latex particles is described for example in EP 80 614 A2, EP 227 054 A2 and EP 246 446 A2.

The term "associated" has a wide meaning and includes, for example, covalent and noncovalent linkage, direct and indirect linkage, adsorption onto a surface and entrapment in a recess or a cavity, etc. In the case of a covalent linkage, the antibodies are linked via a chemical bond to the solid phase or to a component of a signal-generating system. Examples of a noncovalent linkage are surface adsorption, entrapment in cavities or linkage of two specific binding partners. Besides direct linkage to the solid phase or the component of a signal-generating system, it is possible for the antibodies also to be linked indirectly to the solid phase or the label via specific interaction with other specific binding partners (see, e.g. EP 411 945 A2). This is to be illustrated in detail by means of examples: the biotinylated antibody can be linked to the label via label-bound avidin; or a fluorescein-antibody conjugate can be linked to the solid phase via solid phase-bound anti-fluorescein antibodies; or the antibody can be linked to the solid phase or the label via immunoglobulin-binding proteins.

The antibodies of the invention are suitable for use in methods for the quantitative or qualitative determination of the prothrombin fragment F2/F1+2 in a biological sample from a subject, preferably in a patient's blood or plasma sample. The present invention therefore further relates to a method for determining the prothrombin fragment F2/F1+2 in a sample, where the sample is brought into contact with an antibody fragment with specificity for the carboxy-terminal neoepitope of the prothrombin fragment F2/F1+2 to form an immune complex with the prothrombin fragment F2/F1+2 present in the sample. The sample is additionally brought into contact with an antibody of the invention or a fragment thereof which binds to the immune complex but not to the prothrombin fragment F2/F1+2 alone and not to the antibody fragment with specificity for the carboxy-terminal neoepitope of the prothrombin fragment F2/F1+2 alone, and the amount of the bound immune complex is determined. In a preferred embodiment, the sample is brought into contact with an F(ab')$_2$ fragment or with an Fab fragment of the antibody which is formed by the deposited hybridoma cell line DSM ACC2911 in order to form an immune complex with the prothrombin fragment F2/F1+2 present in the sample, and the amount of the immune complex is determined with the aid of an antibody with specificity for this immune complex, preferably with the aid of an antibody which is formed by one of the deposited hybridoma cell lines DSM ACC2912, DSM ACC2913 or DSM ACC2914, or a fragment thereof.

In a method for the quantitative determination of F2/F1+2, the amount or the concentration of F2/F1+2 in the sample is measured. The term "quantitative detection" also includes semiquantitative methods which only estimate the approximate amount or concentration of F2/F1+2 in the sample or can serve only to indicate a relative amount or concentration. A qualitative detection means merely detection of the presence of F2/F1+2 in the sample or indication that the concentration of F2/F1+2 in the sample is below or above a particular or a plurality of particular threshold values.

The invention thus also relates to methods for the quantitative or qualitative detection of F2/F1+2 in a sample and suitable reagents therefor. These methods may be so-called heterogeneous or homogeneous binding assays in which conclusions can be drawn about the presence, absence or amount of F2/F1+2 in a sample through a specific binding of F2/F1+2 to a binding partner. Immunoassays are examples of binding assays.

So-called "heterogeneous binding assays" are characterized by one or more separation steps and/or washing steps. The separation can take place for example by immunoprecipitation, precipitation with substances such as polyethylene glycol or ammonium sulfate, filtration, magnetic removal, attachment to a solid phase. Such a "solid phase" consists of porous and/or nonporous, usually water-insoluble material. It may have a wide variety of shapes, such as, for example: vessel, tube, microtiter plate, bead, microparticle, rod, strip, filter paper or chromatography paper, etc. In heterogeneous binding assays in sandwich format, usually one of the F2/F1+2-specific binding partners is linked to a solid phase and serves to remove the "F2/F1+2-F2/F1+2-specific binding partner" binding complex from the liquid phase, while the other analyte-specific binding partner carries a detectable label (e.g. an enzyme, a fluorescent or chemiluminescent label, etc.) for detecting the binding complex. These assay methods are divided further into so-called one-step sandwich assays in which the two specific binding partners are incubated simultaneously with the sample, and into two-step sandwich assays in which the sample is incubated firstly with the solid phase reagent and, after a separation and washing step, the solid phase-bound binding complex of F2/F1+2 and F2/F1+2-specific binding partner is incubated with the detection reagent.

In "homogeneous binding assays" there is no separation between components of the signal-generating system which are free and those bound to the "F2/F1+2-F2/F1+2-specific binding partner" complex. The assay mixture, which contains the F2/F1+2-specific binding partners, the signal-generating components and the sample, is measured after or even during the binding reaction, without a further separation and/or washing step, and the corresponding measured signal is determined. Examples of homogeneous immunoassays are many turbidimetric and nephelometric methods, where the analyte-specific binding partners used for detection can be associated with latex particles; EMIT® assays; CEDIA® assays; fluorescence polarization immunoassays; luminescent oxygen channeling immunoassays ("LOCI", see EP 515 194 A2; Ullman, E. F. et al. (1994) Proc. Natl. Acad. Sci., 91:5426-5430; Ullman, E. F. et al. (1996) Clinical Chemistry, 42:1518-1526) etc. In a homogeneous sandwich immunoassay, such as, for example, a nephelometric latex assay, the antibody reagents are incubated together with the sample, and the signal is measured during and/or after the incubation, without carrying out a separation or washing step before the measurement. In other words: there is no separation of antibody-bound analyte from free analyte or from antibodies which have bound no analyte.

Homogeneous and heterogeneous binding assays can also be carried out in the form of a so-called "sandwich assay". In this case, the analyte is, for example, in a heterogeneous binding assay, bound by a solid phase-associated analyte-specific binding partner and by an analyte-specific binding partner which is associated with a component of a signal-generating system.

In a homogeneous or heterogeneous "competitive binding assay", sample analyte and reagent analyte (for example a "modified analyte" such as, for example, a labeled or tagged F2/F1+2 or F2/F1+2 fragment) compete for binding to a limited number of analyte-specific binding partners. Examples to illustrate the principle: (i) sample analyte competes with reagent analyte which is associated with a component of a signal-generating system for binding to solid phase-associated analyte-specific binding partners or (ii) sample analyte competes with solid phase-associated analyte (=reagent analyte) for binding to analyte-specific binding partners which are associated with a component of a signal-generating system.

It is also possible to detect F2/F1+2 with the antibodies of the invention for example by methods such as, for example: Western blotting, dot blotting, immunoelectrophoresis, immunofixation electrophoresis, electroimmunodiffusion, immunoprecipitation, radial immunodiffusion, immunofixation, immunochromatography, latex agglutination, turbidimetric or nephelometric assay, homogeneous or heterogeneous binding assay, one- or two-step assay, sandwich assay, indirect assay, competitive assay, point-of-care tests, etc. These and other detection methods are described for example in "Labor und Diagnose", ed. L. Thomas, TH-Books Verlagsgesellschaft mbH, Frankfurt, 1998, chapter 60.

The term "point-of-care tests" or "POC tests" includes tests in which no separate analytical or measurement apparatus is required to carry out the test or evaluate the test. POC tests are based in many cases on immunochromatographic methods, immune complex removal by filtration and/or immunofixation techniques. POC tests are intended in particular for measurements on the spot, e.g. at the hospital bed or at home, for the emergency physician and/or the primary-care physician and less for the large laboratory. POC tests can in particular also be carried out by people having no detailed medical-technical training and experience in the area of laboratory medicine. The term "POC tests" also means for the purposes of this invention so-called home tests or OTC tests which may be carried out by medical laypeople, for example the various pregnancy tests marketed for home use. Other POC tests relate for example to detection of markers of myocardial infarction, drugs, medicaments, markers of infection and inflammation. In many POC tests, specific binding partners are, or become during the carrying out of the test, associated with or on filter or chromatography strips or disks. A positive or negative detection reaction can be linked for example to the appearance or nonappearance of a colored band in a particular test field, and/or the appearance or nonappearance of a particular symbol, e.g. a "+", a "−" and/or the intensity of the particular measured signal.

A POC test for F2/F1+2 can be designed for example as follows: sample and labeled antibody fragments with specificity for the carboxy-terminal neoepitope of the prothrombin fragment F2/F1+2 are applied to a test strip. Examples of suitable labels are colored latex particles, colloidal gold, enzymes etc. If F2/F1+2 is present in the sample there will be formation of F2/F1+2-antibody fragment complexes. These complexes migrate, for example by capillary force, towards a zone in which antibodies of the invention able to bind specifically to the immune complex comprising F2/F1+2 and the antibody fragment with specificity for the carboxy-terminal neoepitope of the prothrombin fragment F2/F1+2 are immobilized, or become immobilized during the test method (e.g. via a biotin-avidin bridge), e.g. in the form of a band. The labeled F2/F1+2-antibody immune complexes are bound in this zone and form a sandwich complex with the immobilized antibodies. The intensity of the label signal is in this case proportional to the F2/F1+2 sample concentration.

Another aspect of the invention is a test kit which comprises at least one reagent which comprises an antibody of the invention which binds to an immune complex comprising prothrombin fragment F2, to which an antibody fragment with specificity for the carboxy-terminal neoepitope of the prothrombin fragment F2/F1+2 is bound, but not to the prothrombin fragment F2 alone and not to the antibody fragment with specificity for the carboxy-terminal neoepitope of the prothrombin fragment F2/F1+2 alone. A preferred test kit comprises an antibody which is formed by one of the deposited hybridoma cell lines DSM ACC2912, DSM ACC2913 or DSM ACC2914. Such a test kit normally comprises all or only some components of a test in packaged form. The antibodies of the invention may be associated for example with one or more solid phases and/or one or more components of a signal-generating system. The test kit may comprise for example standards, controls, and other reagents such as, for example, buffers, washing solutions, measured signal-inducing solutions and/or enzyme substrate; cuvettes; pipettes and/or test instructions.

A test kit of the invention preferably further contains an antibody or an antibody fragment with specificity for the carboxy-terminal neoepitope of the prothrombin fragment F2/F1+2, preferably an F(ab')$_2$ fragment or an Fab fragment of the monoclonal antibody 96-163/04, which is formed by the deposited hybridoma cell line DSM ACC2911.

FIGURE DESCRIPTION

FIG. 1 Calibration plots for quantifying F2/F1+2 in a homogeneous LOCI® assay (see example 3). The measured signals show a proportional relationship to the F1+2 concentration both in a first assay design in which biotinylated immune complex-specific antibodies (BA) were employed in combination with Chemibead-coupled F2/F1+2 neoepitope-specific antibody (CB) (full lines) and in a second assay designed in which a biotinylated F2/F1+2 neoepitope-specific antibody (BA) was employed in combination with Chemibead-coupled immune complex-specific antibodies (CB) (broken lines).

The following examples serve to illustrate the present invention and are not to be understood as restrictive.

Example 1

Preparation of Various Immune Complexes for Use as Immunization Antigens

The following immune complexes were used as immunization antigens:

TABLE 1

| | Immune complex | | | |
|---|---|---|---|---|
| | Prothrombin fragment | F2/F1 + 2 antibody 96-163/04 | Crosslinking | Carrier protein |
| a) | F2/F1 + 2 peptide 15mer | complete | — | — |
| b) | F2/F1 + 2 peptide 15mer | complete | glutaraldehyde | — |
| c) | complete F2 fragment | complete | — | — |
| d) | complete F2 fragment | complete | glutaraldehyde | — |
| e) | complete F2 fragment | Fab fragment | glutaraldehyde | KLH |
| f) | complete F2 fragment | Fab fragment | — | ovalbumin |

Starting Materials:
Prothrombin Fragments Used:
F2/F1+2 Peptide 15 mer
Synthetic peptide consisting of the 14 C-terminal amino acid residues of the human prothrombin fragment F2/F1+2 and an additional amino-terminal cystein residue (sequence: H-Cys-Leu-Asp-Glu-Asp-Ser-Asp-Glu-Glu-Arg-Ala-Ile-Glu-Gly-Arg-OH) (SEQ ID NO:3).
Complete F2 Fragment
A commercially available coagulation factor concentrate (human prothrombin complex) was used as source of prothrombin (Beriplex P/N 500, CSL Behring GmbH, Marburg, Germany) for obtaining a complete F2 fragment (14 kDa). Preparation of the F2 preparation was carried out in the following way:
1. Dissolving of Beriplex in activation buffer (10 mmol Tris, 10 mmol CaCl$_2$, pH 7.5),
2. Coagulation activation using FX-specific RVV-Sepharose (snake venom coupled to carrier material) and incubation with stirring at 37° C.,
3. Removal of the carrier material by means of a suction funnel or centrifugation and subsequent stopping of the coagulation activity using PMSF (phenylmethylsulfonyl fluoride) and addition of sodium citrate,
4. Double absorption/precipitation of the cleavage products with Gla domains using barium chloride and removal by centrifugation,
5. Stabilization, filtration and concentration of the supernatant,
6. Gel filtration of the supernatant using Superdex™ 75 gel material (GE Healthcare Europe GmbH, Germany), running buffer 50 mmol NaHPO$_4$, pH 8.5, use of the F2-containing fractions for further purification,
7. Anion exchange chromatography using Mono Q carrier material (GE Healthcare Europe GmbH, Germany): Buffer A: 50 mmol NaHPO$_4$, pH 8.5

Buffer B: 50 mmol NaHPO$_4$+1 mol NaCl, pH 8.5

Loading of the F2-containing fractions in buffer A, elution with linear salt gradient (0-40% buffer B, 20 column volumes), collection and pooling of the F2-containing fractions, 8. Checking of the purity of the preparation by SDS-PAGE and Western blotting.

Antibodies and Antibody Fragments Used:

The monoclonal antibody F1+2 96-163/04 with specificity for the carboxy-terminal neoepitope of the prothrombin fragment F2/F1+2 was prepared in accordance with the teaching in U.S. Pat. No. 5,830,681 (Hursting et al.). The hybridoma cell line producing the antibody was deposited under the accession number DSM ACC2911. To prepare the Fab fragment, the antibody F1+2 96-163/04 was cleaved with papain by known methods, and the Fab fragment was concentrated.

Preparation of the Immune Complexes:

The immune complexes were prepared by adding the synthetic F2/F1+2 peptide (15mer) or the purified complete F2 fragment in 10-30 molar excess to the monoclonal antibody F1+2 96-163/04 or its Fab fragment, incubating in PBS buffer (pH 7.2) at room temperature for 3 to 3.5 hours, and subsequently purifying the immune complex by chromatography on Sephacryl™ S-100 (GE Healthcare Europe GmbH, Germany).

Crosslinking of Immune Complexes:

Glutaraldehyde was added in a concentration of 0.2% to the mixture, and the mixture was incubated at 2-8° C. for 2 hours. The reaction was stopped by adding NaBH$_4$, and the crosslinked immune complexes were purified on a HiPrep™ desalting column (GE Healthcare Europe GmbH, Germany) (running buffer PBS pH 7.2).

Coupling to Carrier Proteins:

The immune complexes or the crosslinked immune complexes were coupled to keyhole limpet hemocyanin (KLH) or ovalbumin by known routine methods.

Example 2

Preparation and Screening of Antibodies of the Invention

In accordance with the prior art, BALB/c mice were immunized intraperitoneally in each case with 20 µg of immunization antigen (see immune complexes from example 1). Spleen cells of the immunized animals were fused to myeloma cells (Sp2/0), and hybridoma cell lines were established.

Suitable antibodies were identified as follows:

ELISA No. 1: Reactivity with the Immune Complex Consisting of F2 Fragment and the F(ab')$_2$ Fragment of the Monoclonal Antibody F1+2 96-163/04

Microtiter plates coated with the F(ab')$_2$ fragment of the monoclonal antibody F1+2 96-163/04 were incubated with a solution containing F2 fragment (see example 1) in order to form an immune complex of the F(ab')$_2$ fragment of the F2/F1+2-specific antibody and the F2 fragment.

ELISA No. 2: Reactivity with the F2 Fragment Alone

Microtiter plates were coated with the purified F2 fragment (see example 1).

ELISA No. 3: Reactivity with the F(ab')$_2$ Fragment of the Monoclonal Antibody F1+2 96-163/04 Alone Microtiter plates were coated with the F(ab')$_2$ fragment of the F2/F1+2-specific antibody 96-163/04.

100 µl of cell culture supernatant (dilution 1:2) were pipetted into each well of the coated microtiter plates and incubated at +15 to +25° C. for one hour. After the plate had been washed twice with washing solution-POD (OSEW; Siemens Healthcare Diagnostics Products GmbH, Marburg, Germany), 100 µl of anti-mouse IgG/Fc-POD conjugate (peroxidase conjugate, Sigma-Aldrich GmbH, Germany, Prod. No. A0168) were pipetted into each well and incubated at +15 to +25° C. for one hour. After the plate had been washed twice more, 100 µl of chromogen TMB solution (tetramethylbenzidine solution, Siemens Healthcare Diagnostics Products GmbH, Marburg, Germany) were pipetted into each well and incubated at +15 to +25° C. for a further 30 minutes. After the incubation, 100 µl of stop solution POD (Siemens Healthcare Diagnostics Products GmbH, Marburg, Germany) were pipetted into each well, and the microtiter plate was evaluated at 450 nm in a Tecan Sunrise absorbance reader (Tecan Deutschland GmbH, Crailsheim, Germany).

The cell lines whose cell culture supernatants showed a good reactivity with the immune complex (ELISA No. 1) and a minimal or no reactivity with the individual components (ELISA Nos. 2 and 3) were cloned, and larger amounts of antibody were purified from these clones. The concentration of the purified antibodies was adjusted to 1 or 0.1 µg/ml and assayed in ELISAs Nos. 1 to 3.

The results are shown in tables 2 (antibody concentration 1 µg/ml) and 3 (antibody concentration 0.1 µg/ml). The values of the extinction at 450 nm are indicated as measured data.

TABLE 2

| MAb | Group No. | ELISA No. 1 | ELISA No. 2 | ELISA No. 3 |
|---|---|---|---|---|
| 2006-140/0651 | 1 | 3.961 | 0.038 | 0.511 |
| 2006-175/024 | 1 | 2.761 | 0.028 | 0.108 |
| 2006-188/044 | 1 | 3.906 | 0.027 | 0.186 |
| 2006-188/069 | 1 | 3.848 | 0.029 | 0.233 |
| 2006-188/086 | 1 | 3.918 | 0.036 | 0.174 |
| 2006-188/0143 | 1 | 3.970 | 0.031 | 0.387 |
| 2006-209/09 | 1 | 3.819 | 0.030 | 0.166 |
| 2006-216/04 | 1 | 1.940 | 0.024 | 0.230 |
| Prothr. 195/097 | 2 | 4.103 | 3.570 | 0.135 |
| 96-163/04 | 3 | 0.923 | 1.921 | 0.112 |
| 95-332/03 | 3 | 0.290 | 3.552 | 0.097 |
| CRP 268/094 | 4 | 0.062 | 0.027 | 0.099 |
| Background | — | 0.082 | 0.034 | 0.097 |

TABLE 3

| MAb | Group No. | ELISA No. 1 | ELISA No. 2 | ELISA No. 3 |
|---|---|---|---|---|
| 2006-140/0651 | 1 | 3.645 | 0.025 | 0.135 |
| 2006-175/024 | 1 | 1.490 | 0.034 | 0.107 |
| 2006-188/044 | 1 | 3.808 | 0.034 | 0.099 |
| 2006-188/069 | 1 | 3.779 | 0.031 | 0.121 |
| 2006-188/086 | 1 | 3.835 | 0.024 | 0.107 |
| 2006-188/0143 | 1 | 3.795 | 0.025 | 0.132 |
| 2006-209/09 | 1 | 3.171 | 0.027 | 0.110 |
| 2006-216/04 | 1 | 1.548 | 0.020 | 0.102 |
| Prothr. 195/097 | 2 | 3.534 | 1.850 | 0.102 |
| 96-163/04 | 3 | 0.174 | 0.615 | 0.096 |
| 95-332/03 | 3 | 0.096 | 1.203 | 0.096 |
| CRP 268/094 | 4 | 0.081 | 0.025 | 0.101 |
| Background | — | 0.082 | 0.034 | 0.097 |

The tested monoclonal antibodies were divided into groups for improved clarity:

Group 1: antibodies of the invention with specificity for the immune complex consisting of F2 fragment and the F(ab')$_2$ fragment of the F2/F1+2 neoepitope-specific antibody F1+2 96-163/04;

Group 2: prothrombin-specific antibody which binds to an epitope on the N-terminal half of the F2 fragment (see EP 1 541 676 A1, example 2d) and e), hybridoma cell line deposited under accession number DSM ACC2607), included as control;

Group 3: monoclonal antibodies with specificity for the carboxy-terminal neoepitope of the prothrombin fragment F2/F1+2, prepared in accordance with the teaching in U.S. Pat. No. 5,830,681 (Hursting et al.), included as control;

Group 4: monoclonal antibody alien to the F2/F1+2 system, included as negative control.

The antibodies of the invention of group 1 show the desired properties of a monoclonal antibody directed against the immune complex, namely reactivity which is as good as possible with the complex in ELISA No. 1, but only minimal or no reaction in ELISA Nos. 2 and 3.

Example 3

Homogeneous LOCI® Assay for Quantifying F2/F1+2

The LOCI® technology used here is based on a chemiluminescent compound coupled on latex particles (Chemibeads, CB) and a photosensitizer coupled on latex particles (Sensibeads, SB) being brought through binding to an analyte into a spatial proximity such that singlet oxygen, which is generated by the photosensitizer, can excite the chemiluminescent compound. The amount of chemiluminescence generated correlates with the amount of analyte. Dependence of the signal on the F1+2 concentration was shown using the LOCI® technology in a homogeneous immunological assay design.

For a first assay design, the immune complex-specific antibodies 2006-175/024 (from DSM ACC 2912), 2006-188/044 (from DSM ACC 2913) or 2006-188/069 (from DSM ACC 2914) were coupled on Chemibeads. Streptavidin-coated Sensibeads were employed as second component. The biotinylated F2/F1+2 neoepitope-specific antibody 96-163/04 (from DSM ACC2911) was employed as third component.

For a second assay design, the F2/F1+2 neoepitope-specific antibody 96-163/04 (from DSM ACC2911) was coupled on Chemibeads. Streptavidin-coated Sensibeads were employed as second component. The biotinylated immune complex-specific antibodies 2006-175/024 (from DSM ACC 2912), 2006-188/044 (from DSM ACC 2913) or 2006-188/069 (from DSM ACC 2914) were employed as third component.

To quantify the F1+2 concentration, a plasma sample was mixed with the two reagents (Chemibeads and biotinylated antibody) and incubated at 37° C. for 220 seconds. The Sensibeads were then added as further signal component and mixed. This was followed by an additional incubation at 37° C. for 360 seconds. The chemiluminescence was then measured in a LOCI reader.

A standard plot was constructed for quantifying the F2/F1+2 concentration in human plasma samples. For this purpose, F1+2 was adjusted to a defined concentration of 5000 pmol/l in a suitable buffer. Serial dilutions of this stock solution were made and analyzed as described above. Plotting the F1+2 concentration (X axis) against the measured signal heights provides a calibration plot. As is evident from FIG. 1, the generated signal in the two different assay designs is proportional to the F1+2 concentration in the sample, which makes it possible to quantify the F1+2 concentration.

Further investigations have shown that no high-dose hook effect was found up to a concentration of 1 600 000 pmol/l F1+2 with the assay designs chosen here. An incorrectly low determination of the analyte is thus virtually precluded.

The invention claimed is:

1. An isolated immune complex comprising an antibody fragment and a peptide, wherein:
   the peptide includes at least a complete prothrombin fragment F2;
   the carboxy terminus of the complete prothrombin fragment F2 of the peptide is bound to the antibody fragment;
   the antibody fragment has specificity for a carboxy-terminal neoepitope of the prothrombin fragment F2 and/or fragment F1+2; and
   wherein the antibody fragment is a fragment of a monoclonal antibody made by hybridoma cell line DSM ACC 2911.

2. The immune complex of claim 1, wherein the antibody fragment is a Fab, Fab', F(ab')$_2$, or Fv fragment.

3. The immune complex of claim 1, wherein the immune complex is coupled to a carrier protein.

4. The immune complex of claim 3, wherein the carrier protein is keyhole limpet hemocyanin.

5. The immune complex of claim 1, wherein the immune complex is crosslinked with an aldehyde.

6. A method for preparing a monoclonal antibody comprising:
   (a) immunizing an animal with the immune complex of claim 1 as an immunizing antigen;
   (b) preparing a hybridoma cell line from the animal; and
   (c) recovering the monoclonal antibody from the hybridoma cell line,
   wherein the monoclonal antibody is specific for the immune complex but does not bind to either the F2 fragment alone, the F1+2 fragment alone, or the antibody fragment alone.

7. A monoclonal antibody, wherein the monoclonal antibody binds to the immune complex of claim 1, but does not bind to the complete prothrombin fragment F2 alone, and does not bind to the antibody fragment with specificity for the carboxy-terminal neoepitope of a prothrombin fragment F2 and/or fragment F1+2 alone.

8. The monoclonal antibody of claim 7, wherein the monoclonal antibody is produced by hybridoma cell line DSM ACC2912, DSM ACC2913, or DSM ACC2914.

9. The monoclonal antibody of claim 7, wherein the monoclonal antibody is linked to a component of a signal-generating system.

10. The monoclonal antibody of claim 7, wherein the monoclonal antibody is linked to a solid phase.

11. A hybridoma cell line, wherein the hybridoma cell line produces the monoclonal antibody of claim 7.

12. The hybridoma cell line of claim 11, wherein the hybridoma cell line is deposited at DSMZ under accession number DSM ACC2912, DSM ACC2913, or DSM ACC2914.

13. A reagent comprising the monoclonal antibody of claim 7 or an antigen-binding fragment thereof.

14. A test kit comprising the reagent of claim 13.

15. A method for determining an amount or a concentration of prothrombin fragment F2 and/or fragment F1+2 in a sample, comprising:
   (a) contacting the sample with a monoclonal antibody made by hybridoma cell line DSM ACC 2911 or an antibody fragment of the monoclonal antibody made by hybridoma cell line DSM ACC 2911 with specificity for a carboxy-terminal neoepitope of the prothrombin fragment F2 and/or fragment F1+2 to form an immune complex with the prothrombin fragment F2 and/or fragment F1+2 present in the sample;
   (b) contacting the immune complex with the monoclonal antibody of claim 7 or an antigen-binding fragment thereof to form a bound immune complex; and
   (c) conducting a binding assay to determine an amount of the bound immune complex, thereby determining the amount or the concentration of prothrombin fragment F2 and/or fragment F1+2 in the sample.

16. An isolated immune complex comprising an antibody fragment and a peptide, wherein
   the peptide includes at least a complete prothrombin fragment F2;
   a carboxy-terminal neoepitope of the complete prothrombin fragment F2 of the peptide is bound to the antibody fragment;
   the antibody fragment has specificity for the carboxy-terminal neoepitope of the prothrombin fragment F2 and/or fragment F1+2;
   the immune complex is an immunizing antigen that is capable of generating an antibody that binds to the immune complex but does not bind to either the F2 fragment alone, the F1+2 fragment alone, or the antibody fragment alone; and
   wherein the antibody fragment is a fragment of a monoclonal antibody made by hybridoma cell line DSM ACC 2911.

17. A hybridoma cell line, wherein
   the hybridoma cell line produces a monoclonal antibody;
   the monoclonal antibody binds to an isolated immune complex comprising an antibody fragment and a peptide;
   the peptide includes at least a complete prothrombin fragment F2;
   a carboxy-terminal neoepitope of the complete prothrombin fragment F2 of the peptide is bound to the antibody fragment;
   the antibody fragment has specificity for the carboxy-terminal neoepitope of the prothrombin fragment F2 and/or fragment F1+2;
   the immune complex is an immunizing antigen that is capable of generating an antibody that binds to the immune complex but does not bind to either the F2 fragment alone, the F1+2 fragment alone, or the antibody fragment alone;
   the monoclonal antibody does not bind to the complete prothrombin fragment F2 alone, and does not bind to the antibody fragment with specificity for the carboxy-terminal neoepitope of a prothrombin fragment F2 and/or fragment F1+2 alone; and
   wherein the hybridoma cellline is deposited at DSMZ under accession number DSM ACC2912, DSM ACC2913, or DSM ACC2914.

18. A monoclonal antibody, wherein
   the monoclonal antibody binds to an isolated immune complex comprising an antibody fragment and a peptide, wherein
   the peptide includes at least a complete prothrombin fragment F2;
   a carboxy-terminal neoepitope of the complete prothrombin fragment F2 of the peptide is bound to the antibody fragment;
   the antibody fragment has specificity for the carboxy-terminal neoepitope of the prothrombin fragment F2 and/or fragment F1+2;
   the immune complex is an immunizing antigen that is capable of generating an antibody that binds to the immune complex but does not bind to either the F2 fragment alone, the F1+2 fragment alone, or the antibody fragment alone;

the monoclonal antibody does not bind to the complete prothrombin fragment F2 alone, and does not bind to the antibody fragment with specificity for the carboxy-terminal neoepitope of a prothrombin fragment F2 and/or fragment F1+2 alone; and wherein the monoclonal antibody is produced by hybridoma cell line DSM ACC2912, DSM ACC2913, or DSM ACC2914.

* * * * *